United States Patent
Hedberg et al.

(10) Patent No.: US 7,069,076 B2
(45) Date of Patent: *Jun. 27, 2006

(54) MULTI-CHAMBER PACING SYSTEM

(75) Inventors: Sven Erik Hedberg, Kungsängen (SE); Karin Järverud, Solna (SE); Nils Holmström, Järfälla (SE); Anders Björling, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 88 days.

This patent is subject to a terminal disclaimer.

(21) Appl. No.: 10/761,707

(22) Filed: Jan. 21, 2004

(65) Prior Publication Data

US 2004/0193224 A1 Sep. 30, 2004

(30) Foreign Application Priority Data

Mar. 31, 2003 (SE) .................... 0300916

(51) Int. Cl.
*A61N 1/36* (2006.01)
(52) U.S. Cl. .......................... 607/9; 607/27
(58) Field of Classification Search ............ 607/9, 607/27
See application file for complete search history.

(56) References Cited

U.S. PATENT DOCUMENTS

| | | | | |
|---|---|---|---|---|
| 5,591,214 A | | 1/1997 | Lu | |
| 5,694,943 A | * | 12/1997 | Brewer et al. | 600/515 |
| 5,740,811 A | * | 4/1998 | Hedberg et al. | 600/510 |
| 6,144,881 A | * | 11/2000 | Hemming et al. | 607/28 |
| 6,148,234 A | | 11/2000 | Struble | |
| 6,360,126 B1 | * | 3/2002 | Mika et al. | 607/9 |
| 2002/0123769 A1 | * | 9/2002 | Panken et al. | 607/9 |
| 2002/0128687 A1 | * | 9/2002 | Baker et al. | 607/9 |
| 2002/0183792 A1 | * | 12/2002 | Struble | 607/9 |
| 2002/0183798 A1 | * | 12/2002 | Vonk | 607/28 |
| 2003/0004548 A1 | * | 1/2003 | Warkentin | 607/9 |
| 2003/0028222 A1 | * | 2/2003 | Stahmann | 607/9 |
| 2003/0120165 A1 | * | 6/2003 | Bjorling | 600/515 |
| 2003/0144700 A1 | * | 7/2003 | Brown et al. | 607/14 |
| 2004/0260351 A1 | * | 12/2004 | Holmstrom et al. | 607/27 |

* cited by examiner

*Primary Examiner*—Robert E. Pezzuto
*Assistant Examiner*—Eric Bertram
(74) *Attorney, Agent, or Firm*—Schiff Hardin LLP

(57) ABSTRACT

A multi-chamber pacing system has a pulse generator for successively delivering pacing pulses to chambers of a patient's heart, and IEGM signal detectors, having blanking intervals following the delivery of pacing pulses, including sensing circuits for sensing IEGM-signals from each of the heart chambers. Each of said sensed IEGM signals has a generally known morphology. A signal-reconstructing unit reconstructs the IEGM signal from one of the heart chambers in the blanking interval following delivery of a pacing pulse to another heart chamber.

14 Claims, 3 Drawing Sheets

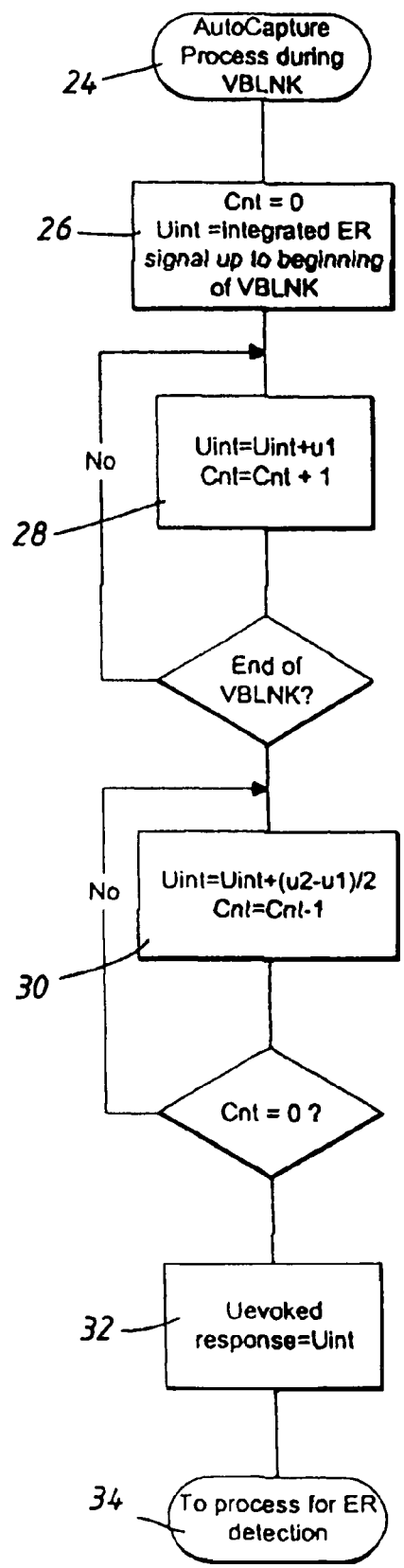

MULTI-CHAMBER PACING SYSTEM

BACKGROUND OF THE INVENTION

1. Field of the Invention

The present invention relates to a multi-chamber pacing system of the type having pulse generator for successively delivering pacing pulses to chambers of a patient's heart, and IEGM signal detectors having blanking intervals following the delivery of pacing pulses and including sensing elements for sensing IEGM signals from each of the heart chambers, with each of the sensed IEGM signals having a generally known morphology.

2. Description of the Prior Art

In the following the term "chambers of the heart" denotes right and left atria as well as right and left ventricles of the heart.

U.S. Pat. No. 6,148,234 disclose a dual site pacing system, either bi-ventricular or bi-atrial, wherein signals are sensed during the refractory period following delivery of stimulation pulses. Pacing pulses are delivered substantially concurrently to both the heart chambers, although it is mentioned that for patients with an intra-atrial block the left atrium may be stimulated up to 90 msec later than the right atrium. If capture is achieved in both chambers, no intrinsic depolarization signals can be sensed during the following refractory period. If, however, the threshold of either heart chamber has risen above the level of the delivered pulses, that chamber will not be captured and will not have a refractory period following that delivery of the pulses. In this case, for patients having a conduction delay from one chamber to the other, the excitation signal from the other chamber will be sensed in the non-captured chamber during the refractory period. Such sensing during the pacemaker refractory period is considered to be the result of loss of capture.

If two heart chambers are stimulated at somewhat different times, one of the chambers will be blanked when the other one is stimulated. Most pacing systems are constructed such that all signal channels are blanked when a stimulation pulse is emitted. Consequently there will be an interruption in sensed IEGM signals. This occurs in all dual or multi chamber pacing systems, e.g. at both bi-ventricular and bi-atrial pacing. If sensed signals are for instance integrated in an evoked response detection time interval from e.g. 4 msec to 50 msec after stimulation to determine evoked response, and if a stimulation of the other chamber takes place at 10 msec after the first stimulation there will be an interruption of the signal in the aforementioned detection time interval.

SUMMARY OF THE INVENTION

An object of the present invention is to provide an improved technique for reconstructing the IEGM signal in a reliable way in multi-chamber pacing, e.g. for presenting the IEGM signal in its entirety to a physician or for printing it out. Such a reconstructed signal is also useful for reliable detection of evoked response.

The above objects are achieved in accordance with the principles of the present invention in a multi-chamber pacing system of the type initially described, that additionally has a signal reconstructing unit that reconstructs the IEGM signal from one of the heart chambers in the blanking interval following delivery of a pacing pulse to another of the heart chambers.

Thus, the basic concept of the present invention is to mathematically reconstruct the IEGM signal sensed in one heart chamber during blanking intervals resulting from stimulation in other chambers. When reconstructing the signal, the knowledge of the general signal morphology is utilized. The pulse generator circuit is controlled to deliver the second pacing pulse with a time delay exceeding the length of the blanking interval following the first one of the two consecutive pacing pulses. It should also be noted that with the present invention it is possible to reconstruct the signal in more than one blanking interval, as may occur in the signal as a result of subsequent stimulations in other chambers of the heart. Such a situation can appear if time delays between the stimulations in different heart chambers are comparatively short.

In an embodiment of the pacing system according to the invention the signal-reconstructing unit selects among several predetermined ways of reconstructing the IEGM signal in the blanking interval with the use of the knowledge of the signal morphology. In this way knowledge about the signal morphology is utilized for selecting the best way of reconstructing the signals in the blanking interval.

If a constant signal level $u_0$, equal to the mean value of the sensed IEGM signal values at the beginning $u_1$ and at the end $u_2$ of the blanking interval, is e.g. integrated during the blanking interval inside an evoked response detection time window for evoked response detection, the result may be somewhat noise sensitive, since it depends only the two samples $u_1$ and $u_2$. To reduce this noise sensitivity, another embodiment of the pacing system according to the invention may be used. In this embodiment, a filter is provided to filter the IEGM signal to produce a reconstructed signal.

In another embodiment of the pacing system according to the invention, with the pacing system having an implantable lead with a tip and a ring electrode and the pulse generator having a case, IEGM signals are measured between the tip electrode and the case and between the ring electrode and the case, respectively. A memory is provided for storing the IEGM signals, and the signal-reconstructing unit reconstructs the IEGM signal measured between the tip electrode and the case, while using the portion of the stored ring electrode-to-case IEGM signal that corresponds to the blanking interval in the reconstructed IEGM signal for the reconstruction within the blanking interval. Even though the ring electrode may be floating in blood and the tip electrode is attached to the myocardium and the tip and ring electrodes have different shapes, the signals will look quite similar. Since the ring electrode is farther away from myocardium than the tip, the signal resulting from depolarization of myocardium will arrive at the tip electrode before it arrives at the ring electrode. Thus the ring-to-case signal will be delayed compared to the tip-to-case signal. If a tip-to-case signal channel is blanked in a time period, information about this blanking period can be found in the ring-to-case signal after a certain time when none of the two signal channels are blanked.

In another advantageous embodiment of the pacing system according to the invention a telemetry arrangement is provided for sending the IEGM signals, including reconstructed signal portions in blanking intervals, to an external programmer for showing IEGMs together with corresponding ECGs on a display and/or printing them out. In this way complete IEGMs, including also blanking intervals, are obtained.

DESCRIPTION OF THE DRAWINGS

FIG. 6 is a flowchart illustrating an example of evoked response signal processing during blanking in the pacing system according to the invention.

DESCRIPTION OF THE PREFERRED EMBODIMENTS

Figure 1:
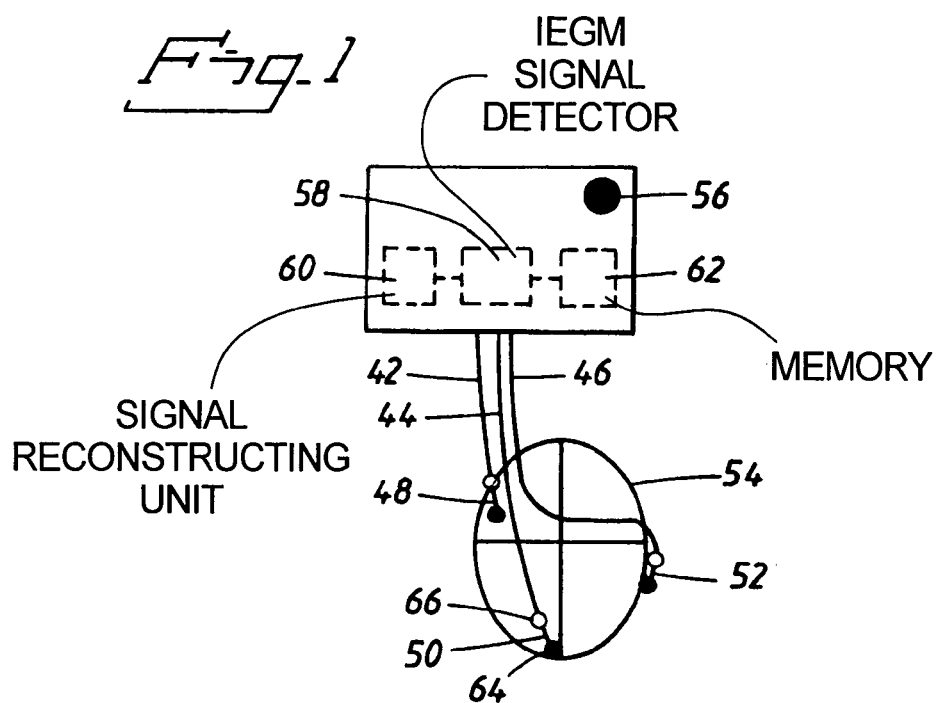
FIG. 1 is a simplified block diagram of an embodiment of the pacing system according to the invention.

FIG. 1 schematically shows a multi-chamber pacing system with leads 42, 44, 46 having bipolar electrodes 48, 50, 52 implanted in right atrium and in the ventricles of a patient's heart 54. The pulse generator case is schematically marked at 56.

Inside the pulse generator case there is an IEGM signal detector 58 with IEGM signal sensing circuits and a signal reconstructing unit 60 and a memory means 62. These components are preferably realized by a microprocessor.

IEGM signals are sensed and integrated by the detector 58. With the signal-reconstructing unit 60 the signal is reconstructed in blanking intervals resulting from delivery of pacing pulses in other heart chambers. In the memory 62 measured complete IEGM signals are stored, such that the reconstructing unit 60 can use the portion of the stored signal that corresponds to the blanking interval. A complete IEGM signal can be measured in advance and stored in the memory 62. IEGM signals alternatively can be measured simultaneously between tip electrode, e.g. the tip electrode 64 in the right ventricle, and the case 56 and between the ring electrode 66 in the right ventricle, and the case 56. The measured IEGM signals are stored in the memory 62. Since the ring-to-case signal is delayed relative to the tip-to-case signal, the signal reconstructing unit 60 reconstructs the IEGM signal measured between the tip electrode 64 and the case 56 while using that portion of the stored ring electrode 66-to-case 56 IEGM signal that corresponds to the blanking interval in the IEGM signal to be reconstructed.

Figure 2:
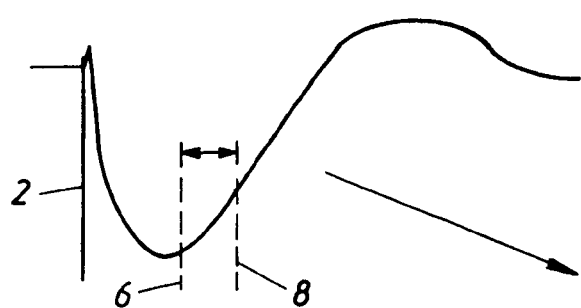
FIGS. 2–5 schematically illustrate IEGM signal portions containing a blanking interval for explaining different reconstructing techniques according to the invention.

FIG. 2 qualitatively shows the simplified appearance of an IEGM signal as a function of time following the delivery of a stimulation pulse 2. A blanking interval 4, resulting from the delivery of a pacing pulse in another heart chamber, is limited by two vertical dashed lines 6,8 in the figure. The blanking time is normally 6–15 msec.

Figure 3:
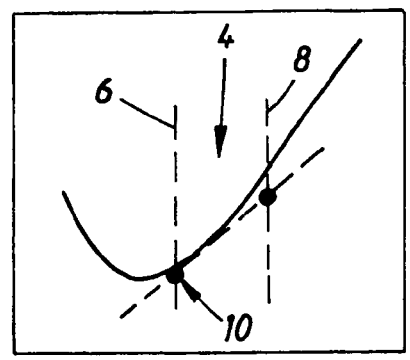

FIG. 3 shows in an enlarged scale a portion of the intracardiac IEGM signal in FIG. 2. FIG. 3 illustrates an example where the signal during the blanking interval 4 is mathematically reconstructed by using the instant slope at the starting point 10 of the blanking interval.

Figure 4:
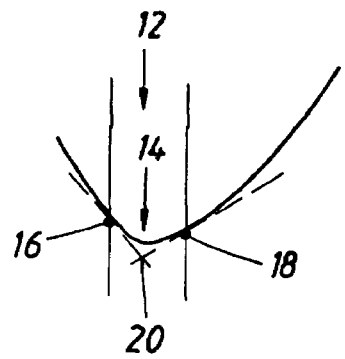

FIG. 4 shows an example with the blanking interval 12 positioned around a minimum 14 in the intracardiac IEGM signal. In this embodiment the signal is reconstructed in the blanking interval by using the instant slopes of the intracardiac signal at the beginning 16 and end 18 of the blanking interval 12 for linear extrapolations of the signal forwardly from the beginning 16 of the blanking interval 12 and rearwardly from the end 18 of the blanking interval respectively. This linear extrapolations meet in an intersection point 20, thus forming a reconstructed signal in the blanking interval 12.

Figure 5:
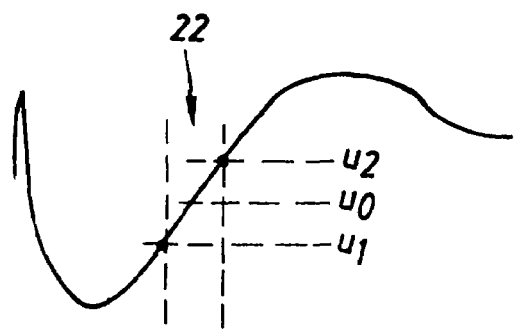

As another alternative the sensed intracardiac signal can be reconstructed or replaced during blanking by a constant signal level $u_0$, e.g. equal to the mean value of the signal values $u_1$ and $u_2$ at the ends of the blanking interval 22, see FIG. 5.

Instead of linear approximations of the signal within the blanking period as described above the signal can be reconstructed by applying a polynomial of suitable degree to the signal by using a number of IEGM signal samples preceding and succeeding the blanking interval.

As can be seen from FIGS. 2–5 the signal smoothly varies with time without any discontinuities. The general morphology or progress of the signal can be determined in advance by introductory measurements and memorized for the subsequent use, cf. the description of FIG. 1 above.

FIG. 6 is a flow chart illustrating an example of signal processing during blanking in a pacing system according to the invention having an evoked response detector. The evoked response signal processing occurs in e.g. a microprocessor-controlled signal procedure known in the art. The example relates to normal autocapture signal processing just interrupted during blanking caused by stimulation in the heart chamber opposite to the considered chamber. The procedure disclosed in FIG. 6 will replace the procedure that would otherwise occur in autocapture signal processing if no blanking had occurred. The input to the flow chart in FIG. 6 is the intracardiac evoked response signal integrated up to the beginning of the blanking interval or blanking point. The flow chart then illustrates the signal processing up to the end of the blanking interval whereafter the integrated evoked response signal is further processed in the normal, well-known way for evoked response detection.

VBLNK, see 24 in FIG. 6, denotes ventricular blanking. Cnt in box 26 in FIG. 6 denotes counter value, and $U_{int}$ denotes integrated ER signal.

In box 28 $U_{int}$ is integrated during VBLNK. The counter value equals the count number of loops, viz. the number of samples during VBLNK.

Box 30 illustrates the addition of the integrated value of estimated mean value of the signal during VBLNK to the integrated ER signal $U_{int}$ up to the beginning of VBLNK.

The resulting evoke response signal $U_{evoked\ response}$, box 32, is then further processed, at 34, for evoked response detection according to well-known technique.

Figure 7:
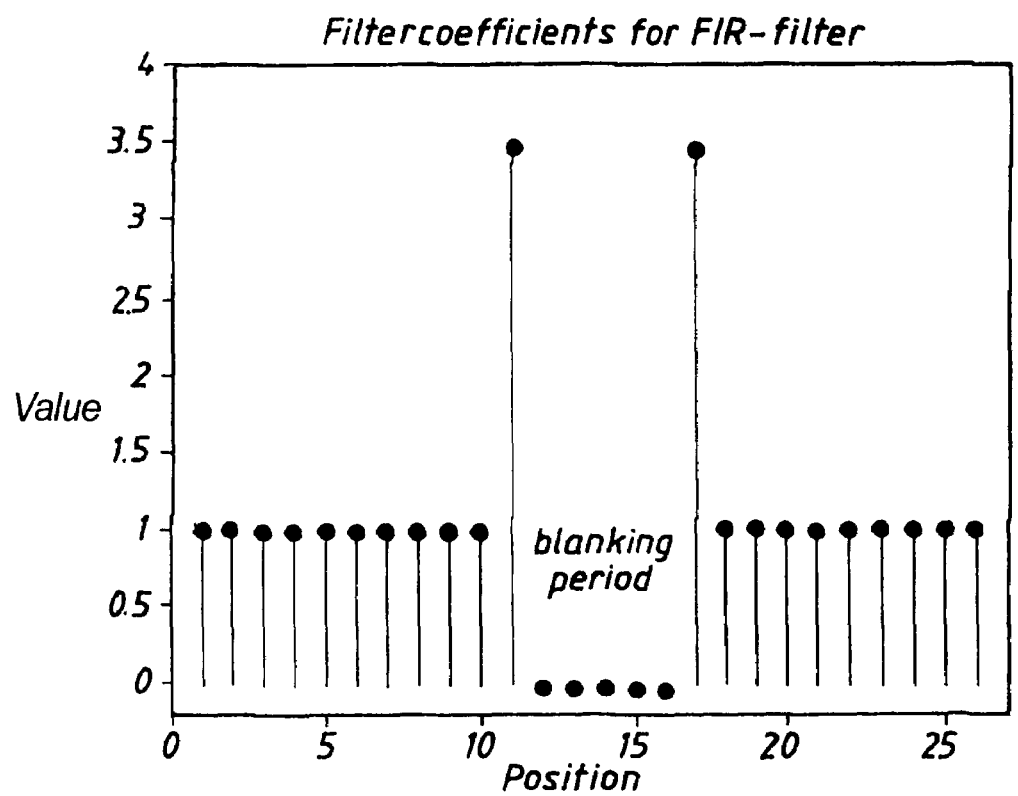
FIG. 7 illustrates another embodiment of reconstruction in the pacing system according the invention.

Another way of viewing the procedure illustrated in FIG. 6 is to consider the samples in the ER window as a mathematical vector. By taking the dot product of this vector and the vector for which samples are depicted in FIG. 7, $U_{evoked\ response}$ is obtained. Given the definition of the product, the value of the integrated linearly interpolated evoked response equals $$U_{evoked\ response} = \sum_{i=1}^{N} u_i \cdot f_i$$

where $u_i$ are the individual voltage samples in the ER window and $f_i$ the (filter) coefficients depicted in FIG. 7.

The value of the filter coefficients immediately preceding and immediately succeeding the blanking period is equal to 1+n/2, where n is the number of samples being blanked.

Although modifications and changes may be suggested by those skilled in the art, it is the intention of the inventors to embody within the patent warranted hereon all changes and modifications as reasonably and properly come within the scope of their contribution to the art.

We claim:

1. A multi-chamber pacing system comprising:
   a pulse generator for generating pacing pulses adapted for delivery to multiple chambers of a heart;
   a plurality of sensing elements adapted to respectively receive and sense IEGM signals from the multiple chambers;
   a control unit connected to said sensing elements for blanking sensing of said IEGM signals in respective blanking intervals following each delivery of a pacing pulse by said pulse generator; and
   a signal reconstructing unit connected to said sensing elements for reconstructing the IEGM signal from one of said multiple chambers in the blanking interval following delivery of one of said pacing pulses to a different chamber among said multiple chambers.

2. A multi-chamber pacing system as claimed in claim 1 wherein said IEGM signal in said blanking interval has a signal morphology, and wherein said signal reconstructing unit identifies said signal morphology and, dependent on said signal morphology, selects a procedure from among a plurality of different predetermined procedures for reconstructing said IEGM signal in said blanking interval.

3. A multi-chamber pacing system as claimed in claim 1 wherein said signal reconstructing unit reconstructs said IEGM signal in said blanking interval by determining an instantaneous slope of said IEGM signal at a beginning of said blanking interval, and by linearly extrapolating said IEGM signal in said blanking interval using said instantaneous slope.

4. A multi-chamber pacing system as claimed in claim 1 wherein said IEGM signal has a minimum in said blanking interval, and wherein said signal reconstructing unit reconstructs said IEGM signal in said blanking interval by determining an instantaneous first slope of said IEGM signal at a beginning of said blanking interval, by determining an instantaneous second slope of said IEGM signal at an end of said blanking interval, and by linearly extrapolating said IEGM signal forwardly from said beginning of said blanking interval in a forward linear extrapolation using said first slope, and rearwardly from said end of said blanking interval in a rearward linear extrapolation using said second slope, to an intersection point of said forward linear extrapolation and said rearward linear extrapolation.

5. A multi-chamber pacing system as claimed in claim 1 wherein said signal reconstructing unit reconstructs said IEGM signal in said blanking interval as a constant equal to an average value of signal values of said IEGM signal at limits of said blanking interval.

6. A multi-chamber pacing system as claimed in claim 1 wherein said signal reconstructing unit reconstructs said IEGM signal in said blanking interval using a plurality of IEGM signal values preceding said blanking interval and succeeding said blanking interval, according to a polynomial of a predetermined degree.

7. A multi-chamber pacing system as claimed in claim 1 wherein said signal reconstructing unit includes a filter, and wherein said signal reconstructing unit reconstructs said IEGM signal in said blanking interval by filtering said IEGM signal with said filter in a filtration time interval having a predetermined duration, said filtration time interval containing said blanking interval.

8. A multi-chamber pacing system as claimed in claim 7 wherein said filter is an FIR filter having filter coefficients equal to zero in said blanking interval.

9. A multi-chamber pacing system as claimed in claim 1 comprising a memory accessible by said signal reconstructing unit, said signal reconstructing unit storing a complete IEGM signal obtained in advance of said blanking interval, and wherein said signal reconstructing unit reconstructs said IEGM signal in said blanking interval using the stored IEGM signal from said memory.

10. A multi-chamber pacing system as claimed in claim 1 comprising at least one implantable lead having a tip electrode and a ring electrode, said electrode lead being connected to said pulse generator and to said sensing elements, and said multi-chamber pacing system further comprising a housing containing said pulse generator, said sensing elements and said signal reconstructing unit, and wherein said sensing elements measure said IEGM signals in the respective chambers between said tip electrode and said housing and between said ring electrode and said housing, and wherein said multi-chamber pacing system comprises a memory, accessible by said signal reconstructing unit, in which said IEGM signals are stored, and wherein said signal reconstructing unit reconstructs said IEGM signal measured between said tip electrode and said housing using a portion of the stored IEGM signal measured between the ring electrode and the housing, which corresponds to the blanking interval for the IEGM signal measured between the tip electrode and the housing.

11. A multi-chamber pacing system as claimed in claim 1 comprising a housing, adapted for intracorporeal implantation, containing said pulse generator, said sensing elements and said signal reconstructing unit, and wherein said multi-chamber pacing system comprises a telemetry arrangement and an external programmer, said telemetry arrangement transmitting said reconstructed IEGM signals extracorporeally to said programmer.

12. A multi-chamber pacing system as claimed in claim 11 wherein said programmer comprises a display for presenting a visual display of said reconstructed IEGM signals, together with corresponding ECG signals.

13. A multi-chamber pacing system as claimed in claim 11 wherein said programmer comprises a printer for printing out said reconstructed IEGM signals together with corresponding ECG signals.

14. A multi-chamber pacing system as claimed in claim 1 wherein said one of said chambers is a first chamber and wherein said other, different chamber is a second chamber, and comprising a first evoked response detector for said first chamber and a second evoked response detector for said second chamber, said first evoked response detector operating with an evoked response detection time window that occurs after delivery of a pacing pulse from said pulse generator to said first chamber and that contains the blanking interval resulting from delivery of said pacing pulse to said second chamber, and said second evoked response detector operating with an evoked response detection time window that occurs after delivery of a pacing pulse to said second chamber, and wherein said first evoked response detector detects an evoked response in said first chamber by integrating the reconstructed IEGM signal occurring in said evoked response detection time window of said first evoked response detector, and wherein said second evoked response detector detects an evoked response in said second chamber by integrating the IEGM signal occurring in said evoked response detection time window of said second evoked response detector.

* * * * *